United States Patent
Liao et al.

(10) Patent No.: US 8,884,258 B1
(45) Date of Patent: Nov. 11, 2014

(54) ULTRAVIOLET LIGHT SOURCE AND METHODS

(71) Applicant: Rayvio Corporation, Livermore, CA (US)

(72) Inventors: Yitao Liao, Redwood City, CA (US); Robert C. Walker, Redwood City, CA (US)

(73) Assignee: Rayvio Corporation, Redwood City, CA (US)

( * ) Notice: Subject to any disclaimer, the term of this patent is extended or adjusted under 35 U.S.C. 154(b) by 0 days.

(21) Appl. No.: 13/757,702

(22) Filed: Feb. 1, 2013

(51) Int. Cl.
*A61L 2/10* (2006.01)
*A61L 2/08* (2006.01)
*A61L 2/00* (2006.01)

(52) U.S. Cl.
CPC ............. *A61L 2/10* (2013.01); *A61L 2/0029* (2013.01); *A61L 2/0047* (2013.01); *A61L 2/08* (2013.01)
USPC ................ 250/504 H; 250/504 R; 422/22; 422/24

(58) Field of Classification Search
CPC ........... A61L 2/00; A61L 2/0029; A61L 2/08; A61L 2/10; A51L 2/0047
USPC ....... 250/493.1, 494.1, 504 R, 504 H; 422/22, 422/24
See application file for complete search history.

(56) References Cited

U.S. PATENT DOCUMENTS

2006/0017025 A1 * 1/2006 Jensen ................. 250/504 R
2009/0095906 A1 * 4/2009 Gavner et al. ............ 250/338.1

* cited by examiner

*Primary Examiner* — Nicole Ippolito
(74) *Attorney, Agent, or Firm* — Richard T. Ogawa; Ogawa P.C.

(57) ABSTRACT

A device for providing ultraviolet light includes a shell for a portable device, wherein the shell includes an interior region and an exterior region, wherein the interior region is adapted to be disposed adjacent to the portable device, a power source configured to provide electrical power, a and an ultraviolet light source coupled to the power source and embedded into the exterior region of the shell, wherein the ultraviolet light source is configured to output the ultraviolet light in response to the electrical power.

20 Claims, 4 Drawing Sheets

ULTRAVIOLET LIGHT SOURCE AND METHODS

BACKGROUND OF THE INVENTION

The present invention relates to a mobile communications device and methods of operation. More specifically, embodiments of the present invention relate to a mobile communications device, such as a smart phone, including an ultraviolet light source, and methods of controlling the ultraviolet light source using the smart phone.

The inventor of the present invention is aware of the use of ultraviolet light for disinfectant purposes. Currently, there are few stand-alone products on the market that provide ultraviolet light for cleaning surfaces or purifying water. One such product is a hand held UV wand that is plugged into a wall socket, and waved over surfaces; and another such product is a hand-held unit that runs on batteries, and is inserted to sanitize a bottle of water.

Some drawbacks contemplated by the inventor, to such devices include the high power consumption of such devices limit utility of such devices. For example, surface sanitizers are typically bulky and need to be powered by plugging them into a wall socket; and portable water sanitizers use batteries, but drain them quickly.

Additional drawbacks contemplated by the inventor, to these devices are when the user travels, they are yet another device that the user must remember to bring along. Because of gadget overload, such dedicated ultraviolet light (UV) sources are not believed to be widely adopted.

From the above, it is desired to have an ultraviolet light source without the drawbacks described above.

BRIEF SUMMARY OF THE INVENTION

The present invention relates to a mobile communications device and methods of operation. More specifically, embodiments of the present invention relate to a mobile communications device, such as a smart phone, including an ultraviolet light source, and methods of controlling the ultraviolet light source using the smart phone.

In some embodiments, a case for a smart phone is contemplated having an integrated ultraviolet (UV) light source and a power source, e.g. batteries. In such embodiments the UV light source may be located near one or more holes of the case, or anywhere else, where the camera of a smart phone is located. In some embodiments, power for the UV light may be drawn from the smart phone.

In some embodiments, a smart phone is contemplated having an integrated UV light source. In such embodiments the UV light source may also be located near the camera of a smart phone is located, or anywhere else. In some embodiments, power for the UV light may be drawn from the smart phone.

In some embodiments, application software is installed upon the smart phone, and programs the processor of the smart phone to perform one or more operations. Some operations may include monitoring a camera image, monitoring accelerometers, directing the UV light to turn on and off, and the like. In some examples, the camera image may be monitored to determine where the UV light is directed towards, may be monitored to determine whether the UV light is pointed upwards or downwards, etc. In other examples, the camera image may be used to determine if the UV light is close enough to a surface for disinfectant purposes, or the like.

In some embodiments, accelerometers, gyroscopes, etc. may also be used to determine orientation of the smart phone. In particular, if the UV light of the smart phone is directed upwards, the power may be shut-off from the UV light; while the UV light of the smart phone is directed, e.g. within 45 degrees of downwards, the UV light may be turned on, or the like.

In various embodiments, using data from one or more of these sensors, the smart phone may be programmed to indicate to the user how long to hold the UV light source of the smart phone over a particular surface; when a particular surface is sanitized and when to move the UV light source of the smart phone to a new location; or the like. In addition, the smart phone may be programmed to turn off the UV light upon unsafe usage conditions, e.g. pointing a UV light source upwards at the user, or other users.

According to one aspect of the invention, a device for providing ultraviolet light is disclosed. One device includes a shell for a portable device, wherein the shell includes an interior region and an exterior region, wherein the interior region is adapted to be disposed adjacent to the portable device. An apparatus includes a power source configured to provide electrical power, and an ultraviolet light source coupled to the power source and embedded into the exterior region of the shell, wherein the ultraviolet light source is configured to output the ultraviolet light in response to the electrical power.

According to another aspect of the invention, a method for providing ultraviolet light is described. One method includes providing a shell having an interior region and an exterior region, wherein the shell comprises an ultraviolet light source embedded into the exterior region of the shell, wherein the ultraviolet light source is configured to output ultraviolet light. A technique may include disposing a portable device adjacent to the interior region within the shell, and powering the ultraviolet light source to cause the ultraviolet light source to output the ultraviolet light to a plurality of surfaces.

Various additional objects, features and advantages of the present invention can be more fully appreciated with reference to the detailed description and accompanying drawings that follow

BRIEF DESCRIPTION OF THE DRAWINGS

In order to more fully understand the present invention, reference is made to the accompanying drawings. Understanding that these drawings are not to be considered limitations in the scope of the invention, the presently described embodiments and the presently understood best mode of the invention are described with additional detail through use of the accompanying drawings in which.

DETAILED DESCRIPTION OF THE INVENTION

Figure 1:
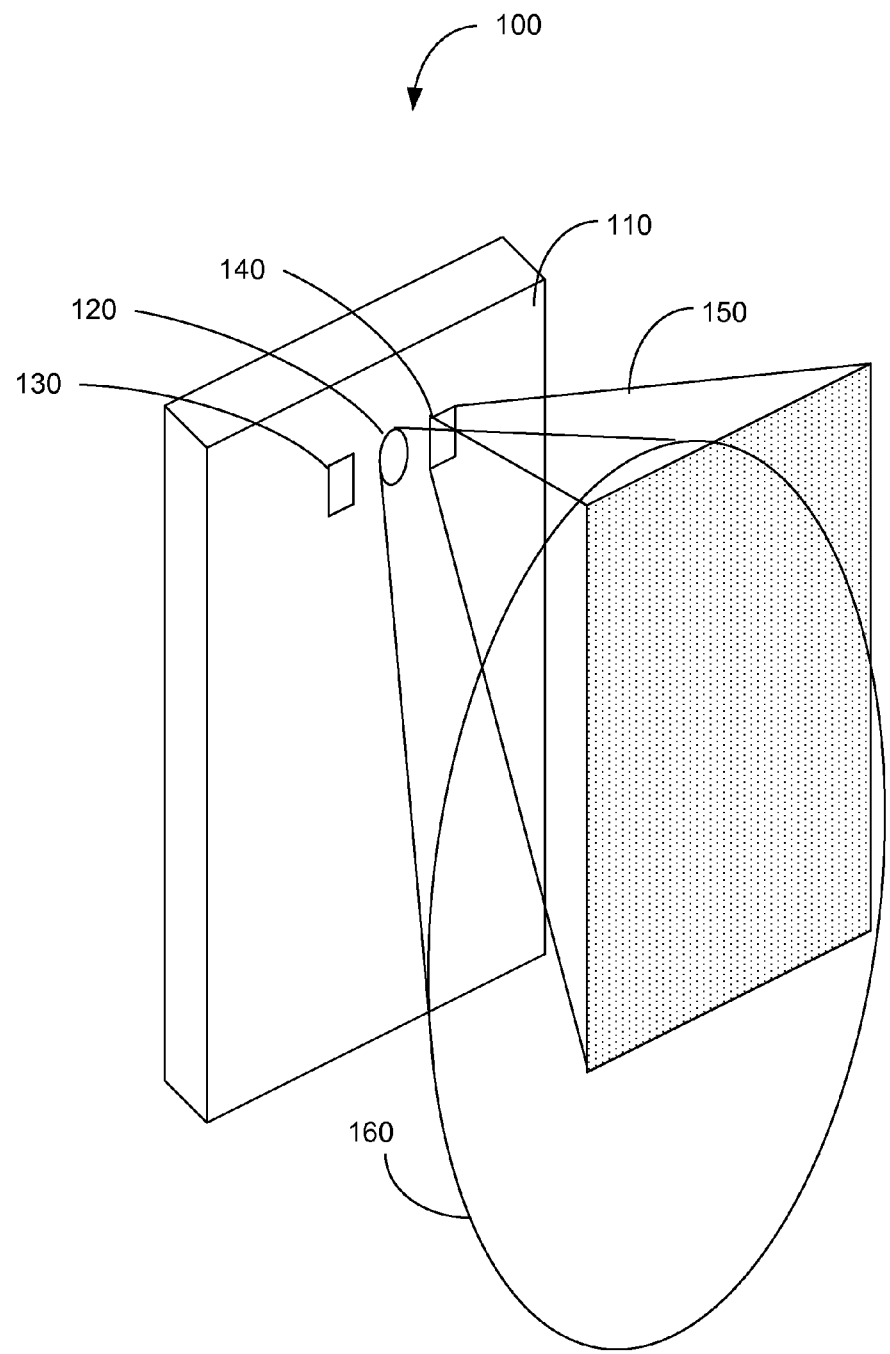
FIG. 1 illustrates an example of various embodiments of the present invention.

FIG. 1 illustrates various embodiments of the present invention. More specifically, FIG. 1 illustrates a hand-held computing device (e.g. smart phone, tablet) 100.

In various embodiments, as illustrated, the back casing 110 of device 100, may include a camera 120, a LED light source (e.g. flash) 130, and a UV light source 140. As seen in FIG. 1, UV light source 140 may be positioned such that light 150 from the UV light source 140 is within a field of view 160 of camera 120. In other embodiments, light 150 may not be within field of view 160. Additionally, in other embodiments, UV light source 140 may be positioned on the side, top, bottom, or the like of smart device 100.

Figure 2:
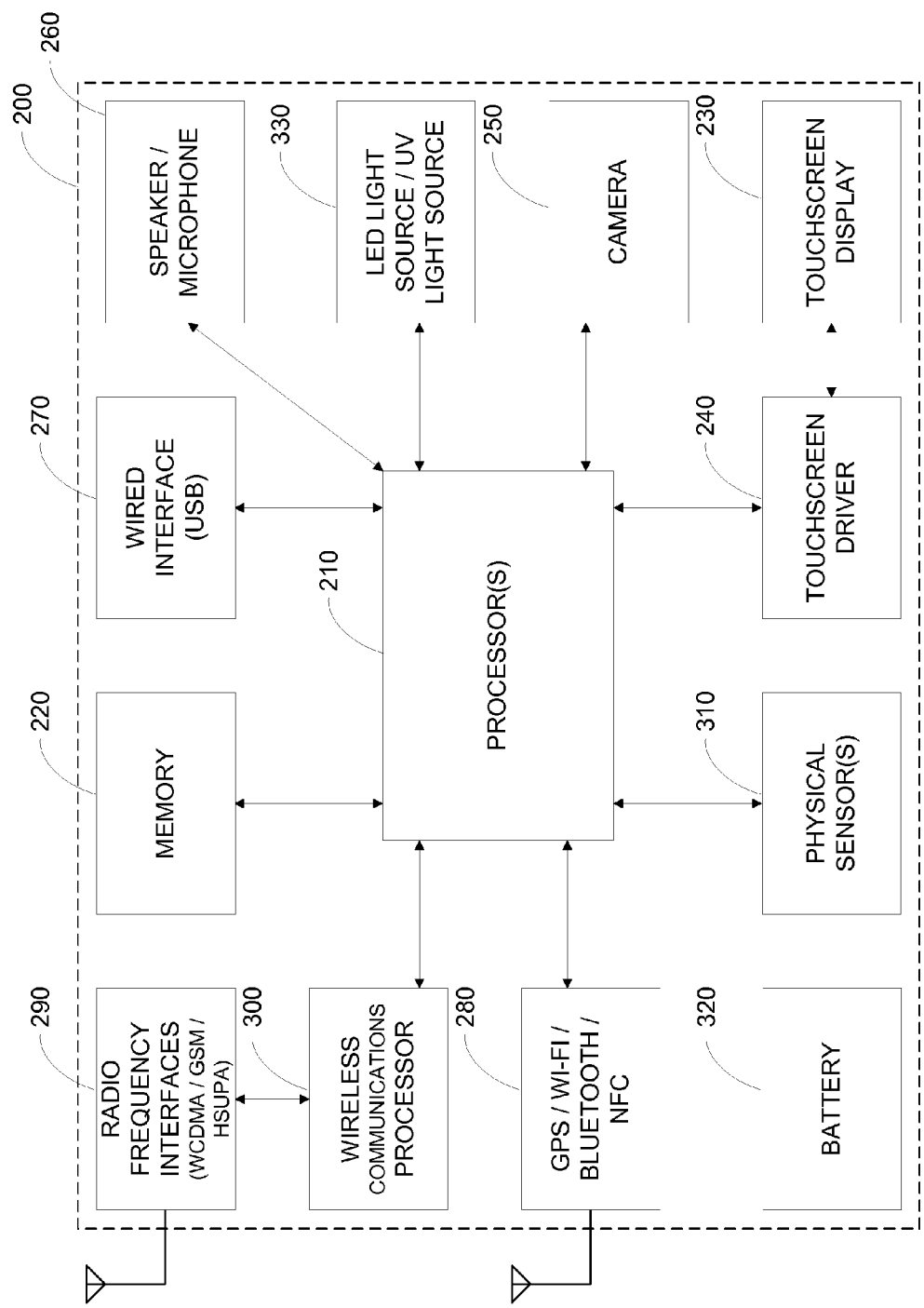
FIG. 2 illustrates a functional block diagram of various embodiments of the present invention.

FIG. 2 illustrates a functional block diagram of various embodiments of the present invention. In FIG. 2, a computing device 200 typically includes an applications processor 210, memory 220, a touch screen display 230 and driver 240, a camera 250, audio input/output devices 260, and the like. Additional communications from and to computing device are typically provided by via a wired interface 270, a GPS/Wi-Fi/Bluetooth interface 280, RF interfaces 290 and processor 300, and the like. Also included in various embodiments are physical sensors 310.

In various embodiments, computing device 200 may be a hand-held computing (smart) device (e.g. Apple iPad, Microsoft Surface, a tablet), a smart phone (e.g. Apple iPhone, Motorola Droid, Google Nexus, Samsung Galaxy S), a portable computer (e.g. netbook, laptop), a media player (e.g. Microsoft Zane, Apple iPod), a reading device (e.g. Amazon Kindle, Barnes and Noble Nook), or the like.

Typically, computing device 200 may include one or more processors 210. Such processors 210 may also be termed application processors, and may include a processor core, a video/graphics core, and other cores. Processors 210 may be a processor from Apple (A6), Intel (Atom), NVidia (Tegra 3), Marvell (Armada), Qualcomm (Snapdragon). Samsung. TI (OMAP), or the like. In various embodiments, the processor core may be an Intel processor, an ARM Holdings processor such as the Cortex-A, -M, -R or ARM series processors, or the like. Further, in various embodiments, the video/graphics core may be an Imagination Technologies processor PowerVR-SGX, -MBX, -VGX graphics, an Nvidia graphics processor (e.g. GeForce), or the like. Other processing capability may include audio processors, interface controllers, and the like. It is contemplated that other existing and/or later-developed processors may be used in various embodiments of the present invention.

In various embodiments, memory 220 may include different types of memory (including memory controllers), such as flash memory (e.g. NOR, NAND), pseudo SRAM, DDR SDRAM, or the like. Memory 220 may be fixed within computing device 200 or removable (e.g. SD, SDHC, MMC, MINI SD, MICRO SD, CF, SIM). The above are examples of computer readable tangible media that may be used to store embodiments of the present invention, such as computer-executable software code (e.g. firmware, application programs), application data, operating system data or the like. It is contemplated that other existing and/or later-developed memory and memory technology may be used in various embodiments of the present invention.

In various embodiments, touch screen display 230 and driver 240 may be based upon a variety of later-developed or current touch screen technology including resistive displays, capacitive displays, optical sensor displays, electromagnetic resonance, or the like. Additionally, touch screen display 230 may include single touch or multiple-touch sensing capability. Any later-developed or conventional output display technology may be used for the output display, such as TFT-LCD, OLED, Plasma, trans-reflective (Pixel Qi), electronic ink (e.g. electrophoretic, electrowetting, interferometric modulating). In various embodiments, the resolution of such displays and the resolution of such touch sensors may be set based upon engineering or non-engineering factors (e.g. sales, marketing). In some embodiments of the present invention, a display output port, such as an HDMI-based port or DVI-based port may also be included.

In some embodiments of the present invention, image capture device 250 may include a sensor, driver, lens and the like. The sensor may be based upon any later-developed or convention sensor technology, such as CMOS, CCD, or the like. In various embodiments of the present invention, image recognition software programs are provided to process the image data. For example, such software may provide functionality such as: facial recognition, head tracking, camera parameter control, image differencing, or the like.

In various embodiments, audio input/output 260 may include conventional microphone(s)/speakers. In some embodiments of the present invention, three-wire or four-wire audio connector ports are included to enable the user to use an external audio device such as external speakers, headphones or combination headphone/microphones. In various embodiments, voice processing and/or recognition software may be provided to applications processor 210 to enable the user to operate computing device 200 by stating voice commands. Additionally, a speech engine may be provided in various embodiments to enable computing device 200 to provide audio status messages, audio response messages, or the like.

In various embodiments, wired interface 270 may be used to provide data transfers between computing device 200 and an external source, such as a computer, a remote server, a storage network, another computing device 200, or the like. Such data may include application data, operating system data, firmware, or the like. Embodiments may include any later-developed or conventional physical interface/protocol, such as: USB 3.0, 3.0, micro USB, mini USB, Firewire, Apple iPod connector, Ethernet, POTS, or the like. Additionally, software that enables communications over such networks is typically provided.

Figure 3:
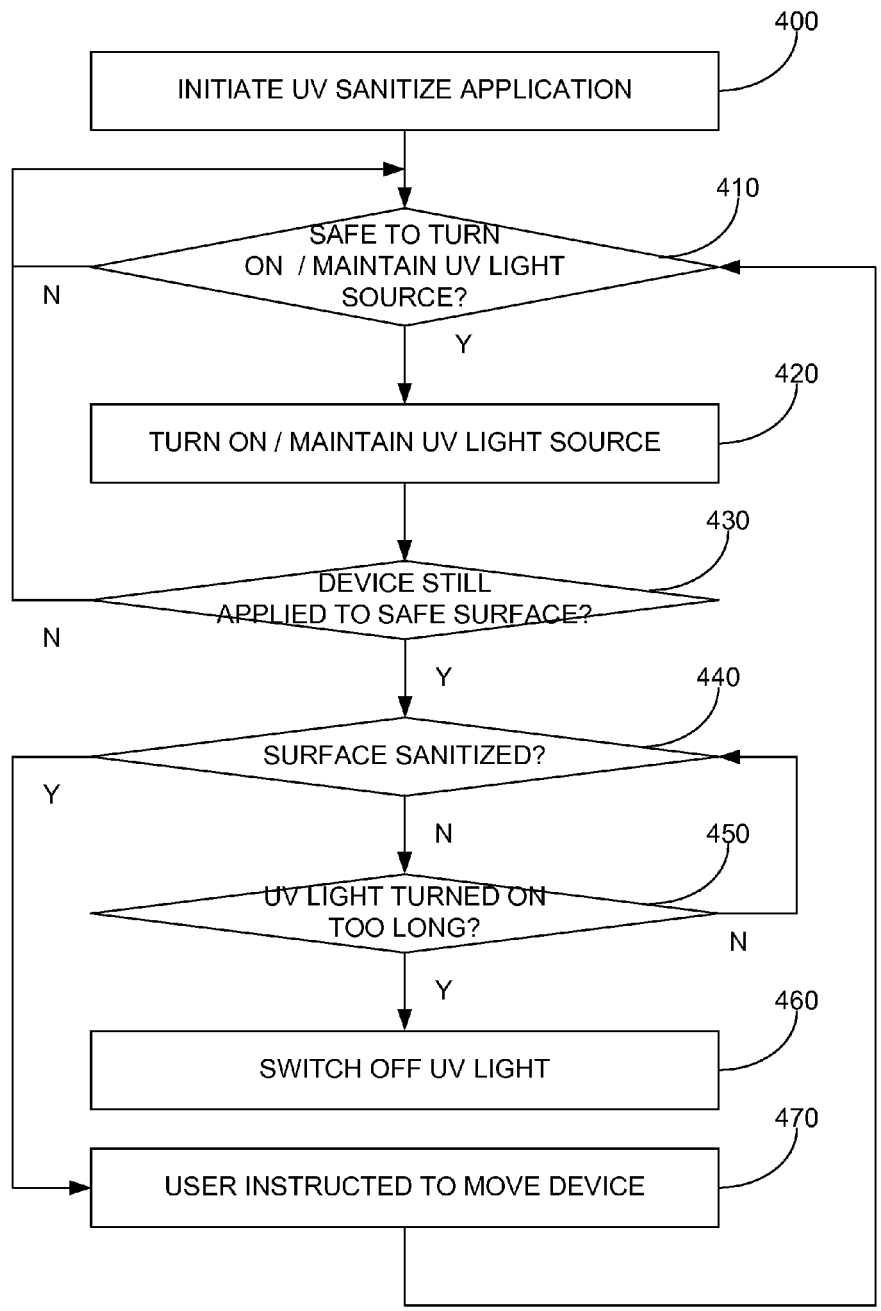
FIG. 3 illustrate block diagrams of flow processes according to various embodiments of the present invention.

In various embodiments, a wireless interface 280 may also be provided to provide wireless data transfers between computing device 200 and external sources, such as computers, storage networks, headphones, microphones, cameras, or the like. As illustrated in FIG. 3, wireless protocols may include Wi-Fi (e.g. IEEE 802.11a/b/g/n, WiMax), Bluetooth, IR and the like.

GPS receiving capability may also be included in various embodiments of the present invention, however is not required. As illustrated in FIG. 2, GPS functionality is included as part of wireless interface 280 merely for sake of convenience, although in implementation, such functionality is currently performed by circuitry that is distinct from the Wi-Fi circuitry and distinct from the Bluetooth circuitry.

Additional wireless communications may be provided via RF interfaces 290 and drivers 300 in various embodiments. In various embodiments, RE interfaces 290 may support any future-developed or conventional radio frequency communications protocol, such as CDMA-based protocols (e.g. WCDMA), GSM-based protocols, HSUPA-based protocols, or the like. In the embodiments illustrated, driver 300 is illustrated as being distinct from applications processor 210. However, in some embodiments, these functionality are provided upon a single IC package, for example the Marvel PXA330 processor, and the like. It is contemplated that some embodiments of computing device 200 need not include the RF functionality provided by RE interface 290 and driver 300.

FIG. 2 also illustrates computing device 200 to include physical sensors 310. In various embodiments of the present invention, physical sensors 310 are multi-axis Micro-Electro- Mechanical Systems (MEMS). Such MEMS devices may include accelerometers, gyroscopes, magnetometers, pressure sensors, or the like. In some embodiments of the present invention, conventional physical sensors 310 from Bosch, STMicroelectronics, Analog Devices, Kionix or the like may be used. In various embodiments, these MEMS devices, as well as most, if not all of the above-described electronic devices, are powered by a battery 320.

In various embodiments, any number of future developed or current operating systems may be supported, such as IOS (e.g. 6.0), WindowsMobile (e.g. 8), Google Android, Symbian, or the like. In various embodiments of the present invention, the operating system may be a multi-threaded multi-tasking operating system. Accordingly, inputs and/or outputs from and to touch screen display 230 and driver 240 and inputs/or outputs to physical sensors 310 may be processed in parallel processing threads. In other embodiments, such events or outputs may be processed serially, or the like. Inputs and outputs from other functional blocks may also be processed in parallel or serially, in other embodiments of the present invention, such as camera 250 and physical sensors 310.

In some embodiments, computing device may include a UV light source 330. The UV light source 330 may be embodied as a UV light source being developed by the assignee of the present patent application, RayVio. In other embodiments, UV light source 330 may be utilized.

FIG. 2 is representative of one computing device 200 capable of embodying the present invention. It will be readily apparent to one of ordinary skill in the art that many other hardware and software configurations are suitable for use with the present invention. Embodiments of the present invention may include at least some but need not include all of the functional blocks illustrated in FIG. 2. For example, in various embodiments, computing device 200 may lack image acquisition unit 250, or RF interface 290 and/or driver 300, or GPS capability, or the like. Additional functions may also be added to various embodiments of computing device 200, such as a physical keyboard, an additional camera, a trackball or trackpad, a joystick, or the like. Further, it should be understood that multiple functional blocks may be embodied into a single physical package or device, and various functional blocks may be divided and be performed among separate physical packages or devices.

FIG. 3 illustrates block diagrams of flow processes according to various embodiments of the present invention.

In various embodiments, the user initiates an application upon the smart device to start a UV sanitation process, step 400. In some embodiments, this may include the user tapping upon an application icon of a display of the smart device, the user hitting a physical button on the smart device, a software tinier going off, or the like.

In some embodiments, the smart device determines whether it is safe to turn on or keep on the UV light, step 410. In some embodiments, this may include the smart device monitoring the MEMS sensors, discussed above, to ensure that the UV light of the smart phone is directed towards the ground, e.g. not upwards towards the face of the user. In some embodiments, this may include the smart device monitoring the amount of light reaching the camera. For example, if there is little light reaching a downwards facing camera, but a lot of light reaching an upwards facing camera, it might be assumed that the downwards camera is downwards and adjacent to the surface being sanitized. Accordingly, the downwards facing camera will not detect much light. In various embodiments, the tilt angle of the downwards orientation may vary, for example by +/−10 degrees, +/−45 degrees, or the like; and the amount of light reaching the camera, for the UV light to be turned on may vary within a range, e.g. 0 to 10, 0 to 50, etc. from a scale of 0 to 255, or the like. In still other embodiments, combinations of MEMS sensors and optical detection may be used for this step.

In some embodiments, images from the cameras may be processed by pattern recognition software to provide additional capabilities. In some examples, images from a downwards facing camera (assuming the UV light is also directed downwards) can be used to help determine if the UV light is directed towards a safe surface for sanitization. In some examples, if the downwards facing camera captures an image of a face, animal, skin, or the like, the UV light may be inhibited; if neither the upwards facing camera nor the downwards facing camera recognizes a face, only then can the UV light may be allowed; or the like. In some embodiments, only groups of specific surfaces can be sanitized, after these surfaces are visually identified. As examples, when surfaces with printed letters, e.g. keyboards, magazines, airplane emergency cards are identified by character recognition software, the UV light source may be enabled. In other examples, surfaces to be sanitized may be identified by bar-code, QR code, image, target, or the other such identifier. In such examples, only surfaces bearing such identifiers can be sanitized. In light of the above, one of ordinary skill in the art will recognize many other examples of image recognition that may be used in various embodiments of the present invention.

In various embodiments, if safe, power may be applied to the UV light and one or more timers may be initiated, step 420. In some embodiments, when the UV light is turned on, one or more indicators may be displayed to the user, for example, an auxiliary light may turn on, the display of the smart device may turn blue, or the like.

In various embodiments, while the UV light is positioned over a particular surface, the cameras and/or the MEMS sensors may be used to determine whether the smart phone has moved, step 430. In some embodiments, to sanitize a surface, the surface should be exposed to UV light for a certain amount of time. However, if the user moves the UV light around, a keyboard, for example, regions of the keyboard may not be sufficiently exposed to the UV light. Accordingly, in various embodiments, based upon optical tracking (from camera images), or MEMS sensors, it can be determined where the smart device/UV light is irradiating, in time.

In some embodiments, the timers may be used to determine whether the UV light has exposed a surface a sufficient period of time, step 440, and/or to determine whether the UV light has been powered on for too long, step 450. In the latter case, the UV light may be automatically switched off, step 460. In other embodiments, many other such timers may be used for similar purposes. In various embodiments, the amount of time may vary upon the type of surface to be disinfected, for example, fruit, water, and plastic surfaces are believed to require different exposure times.

In various embodiments, after a particular surface has be exposed to UV light for a sufficient period of time, the user may be visually indicated to move the smart device/UV light to another surface, step 470. In some embodiments, the user may terminate the above process at any time.

Figure 4:
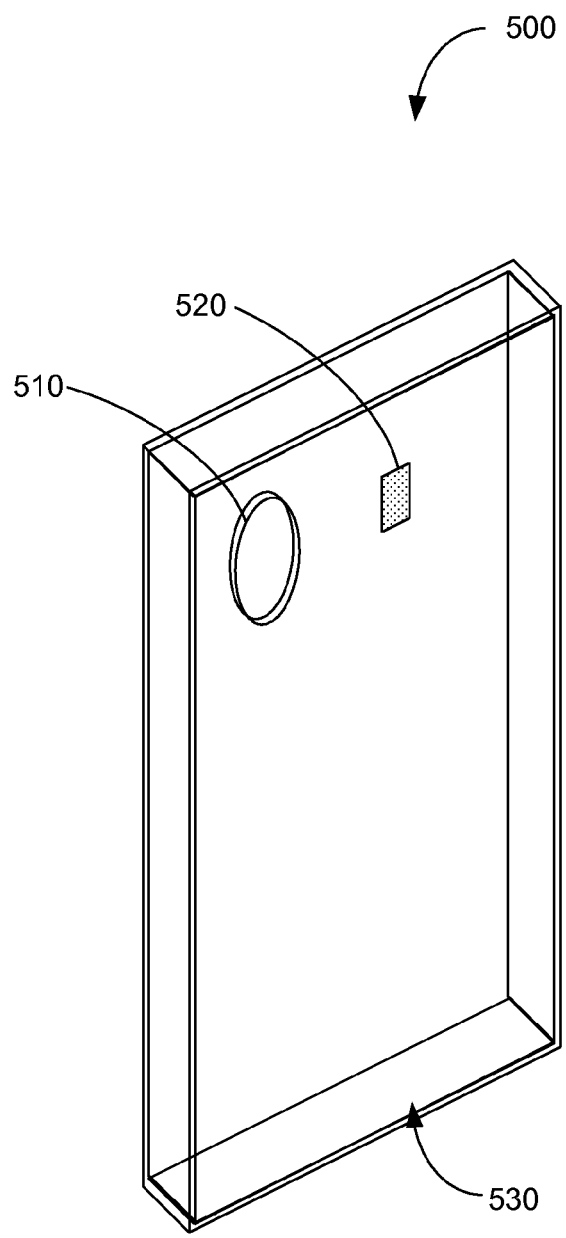
FIG. 4 illustrate an example of various embodiments of the present invention.

FIG. 4 illustrates another embodiment of the present invention. More specifically, FIG. 4 illustrates a protective housing 500 for a smart device, e.g. smart phone.

As illustrated, protective housing 500 may include an opening 510 where the camera of the smart device is positioned. Additionally, housing may include a UV light source 520, typically near opening 510, and a region 530 for a power source, e.g. battery. In some embodiments, a power source, e.g. battery need not be provided within protective housing 500. Instead, in some embodiments, UV light source 520 receives power from a smart device that is nestled within protective housing 500. For example, a plug, or the like may be provided that physically plugs into a port of the smart device and draws power therefrom. In some embodiments, the port may be an I/O port, power port, peripheral port, or other ports. In such embodiments, the smart device may control light from UV light source 520 by selectively applying power over the port.

Input from direct connection, Bluetooth, or the like.

As discussed above, in various embodiments of housing 500, a field of view of UV light source 520 may be positioned within a field of view of a smart device camera. In other embodiments, e.g. relying upon MEMS devices, these field of views may not overlap.

In some embodiments, MEMS acclerometers, or the like may be integrated into protective housing 500

Further embodiments can be envisioned to one of ordinary skill in the art after reading this disclosure. In other embodiments, combinations or sub-combinations of the above disclosed invention can be advantageously made. The block diagrams of the architecture and flow charts are grouped for ease of understanding. However it should be understood that combinations of blocks, additions of new blocks, re-arrangement of blocks, and the like are contemplated in alternative embodiments of the present invention.

The specification and drawings are, accordingly, to be regarded in an illustrative rather than a restrictive sense. It will, however, be evident that various modifications and changes may be made thereunto without departing from the broader spirit and scope of the invention as set forth in the claims.

We claim:

1. A protective case for a portable handheld electronic device comprising:
    a protective shell for the portable handheld device, wherein the protective shell includes an interior region and an exterior region, wherein the interior region is sized and configured to extend to fit snugly over at least a portion of a back of the portable handheld device, wherein the protective shell includes a rear opening where a camera on the back of the portable handheld device is to be located, and wherein the protective shell includes a front opening where a touch screen display on a front of the portable handheld device to be located;
    a power source configured to provide electrical power; and
    an ultraviolet light source coupled to the power source and embedded into the protective shell, wherein the ultraviolet light source is configured to output ultraviolet light in response to the electrical power.

2. The protective case of claim 1 further comprising:
    a sensor configured to determine an orientation of the protective shell with respect to gravity; and
    a light inhibiting portion coupled to the ultraviolet light source and to the sensor, wherein the light inhibiting portion is configured to inhibit output of the ultraviolet light from the ultraviolet light source in response to the orientation of the shell.

3. The protective case of claim 2, wherein the orientation is selected from a group consisting of: upwards, sideways.

4. The protective case of claim 1 wherein the power source is disposed within the shell and comprises a battery.

5. The protective case of claim 1 further comprising the portable handheld electronic device, wherein the portable handheld electronic device is removably disposed within the protective case by a user and is adjacent to the interior region of the protective shell.

6. The protective case of claim 5 wherein the power source is disposed within the portable handheld electronic device.

7. The protective case of claim 5
    wherein the portable handheld electronic device comprises a timer portion and a movement sensor, wherein the movement sensor is configured to determine movement of the portable handheld electronic device, and wherein the timer portion is configured to determine an amount of time the portable handheld electronic device is stationary in response to the movement of the portable handheld electronic device in response to the movement of the portable handheld electronic device, wherein the movement sensor is selected from a group consisting of: an accelerometer and a gyroscope; and
    wherein an amount of time the ultraviolet light source illuminates a particular surface with the ultraviolet light is associated with the amount of time the portable handheld electronic device is stationary.

8. The protective case of claim 7
    wherein the timer portion is configured to determine whether the amount of time the portable handheld electronic device is stationary exceeds a threshold time; and
    wherein the touch screen display of the portable handheld electronic device is configured to output an indicator to the user when the amount of time exceeds the threshold time.

9. The protective case of claim 5
    wherein the ultraviolet light illuminates a particular surface;
    wherein the portable handheld electronic device comprises a timer portion, wherein the camera on the back of the portable handheld electronic device is configured to acquire a plurality of images though the rear opening of the protective shell including images of the particular surface; and
    wherein the timer portion is configured to determine an amount of time the portable handheld electronic device is stationary in response to the plurality of images.

10. The protective case of claim 9
    further comprising determining with a processor in the portable handheld electronic device whether the portable handheld electronic device is stationary in response to the plurality of images.

11. A method for providing ultraviolet light comprising:
    receiving a protective shell having an interior region and an exterior region, wherein the interior region is sized and configured to extend to fit snugly over at least a portion of a back of the portable handheld device, wherein the protective shell includes a rear opening where a camera on the back of the portable handheld device is to be located, wherein the protective shell includes a front opening where a touch screen display on a front of the portable handheld device to be located, wherein the protective shell comprises an ultraviolet light source embedded into the exterior region of the protective shell, wherein the ultraviolet light source is configured to output ultraviolet light;
    disposing the portable handheld electronic device into the interior region within the protective shell; and
    powering the ultraviolet light source to cause the ultraviolet light source to output the ultraviolet light to a plurality of surfaces.

12. The method of claim 11 further comprising:
  determining an orientation of the portable handheld electronic device with respect to gravity with an orientation sensor; and
  inhibiting output of the ultraviolet light from the ultraviolet light source in response to the orientation of the shell.

13. The method of claim 12, wherein the orientation is selected from a group consisting of: upwards, sideways.

14. The method of claim 11 further comprising powering the ultraviolet light source with electrical power from a battery disposed within the protective shell.

15. The method of claim 11 further comprising powering the ultraviolet light source with electrical power from the portable handheld electronic device.

16. The method of claim 15 further comprising:
  displaying an ultraviolet light illumination indicator on a touch screen display of the portable handheld electronic device to a user;
  receiving a selection of an icon by the user on touch screen display of the portable handheld electronic device; and
  inhibiting the electrical power powering the ultraviolet light source in response to the selection of the icon by the user.

17. The method of claim 11
  determining movement of the portable handheld electronic device with a movement sensor;
  determining an amount of time the portable handheld electronic device is stationary; and
  wherein the amount of time the portable handheld electronic device is stationary is associated with an amount of time the ultraviolet light illuminates a particular surface.

18. The method of claim 17 determining whether the amount of time the portable handheld electronic device is stationary exceeds a threshold time; and
  displaying an indicator on a touch screen of the portable handheld electronic device a user when the amount of time exceeds the threshold time.

19. The method of claim 11 further comprising:
  acquiring a plurality of images with the camera on the back of the portable handheld device;
  determining movement of the portable handheld electronic device in response to the plurality of images;
  determining whether one of the plurality of images is associated with a class of images; and
  inhibiting powering the ultraviolet light when one of the plurality of images is determined to be associated with a class of images comprising human faces.

20. A portable handheld electronic device for providing ultraviolet light comprising:
  a housing comprising one or more openings and having a front surface and a rear surface;
  a power source disposed within the housing and configured to provide electrical power;
  a camera disposed within the housing, wherein the camera is directed through the one or more openings on the rear surface, wherein the camera is coupled to the power source, and wherein the camera is configured to acquire a plurality of images;
  a touch-screen display disposed within the housing, wherein the touch-screen display is directed through the one or more openings on the front surface, wherein the touch-screen display is coupled to the power source, wherein the touch-screen display is configured to display one or more images to a user, and wherein the touch-screen display is configured to receive selections of one or more applications on the portable handheld electronic device by the user;
  an ultraviolet light source disposed within the housing, wherein the ultraviolet light source is directed through the one or more openings on the rear surface, wherein the camera is coupled to the power source, and wherein the ultraviolet light source is configured to output the ultraviolet light in response to the electrical power; and
  a processor coupled to the power source, the camera, the touch-screen display, and the ultraviolet light source, wherein the processor is programmed to determine whether to provide the electrical power to the ultraviolet light source in response to the plurality of images acquired by the camera.

\* \* \* \* \*